United States Patent [19]

Dilks, Jr. et al.

[11] 4,448,679

[45] May 15, 1984

[54] APPARATUS AND METHOD FOR SEDIMENTATION FIELD FLOW FRACTIONATION

[75] Inventors: Charles H. Dilks, Jr., Newark; Joseph J. Kirkland; Wallace W. Yau, both of Wilmington, all of Del.

[73] Assignee: E. I. Du Pont de Nemours and Company, Wilmington, Del.

[21] Appl. No.: 326,156

[22] Filed: Nov. 30, 1981

[51] Int. Cl.³ .............................................. B03B 5/62
[52] U.S. Cl. ........................................ 209/155; 494/27; 494/37; 494/38; 494/43
[58] Field of Search ............... 209/1, 155, 208, 209, 209/444, 453; 233/1 A, 14 R, 14 A, 27, 45, 46, 1 E, 16, 21, 26, 28, 40 R

[56] References Cited

U.S. PATENT DOCUMENTS

| | | | |
|---|---|---|---|
| 3,465,956 | 9/1969 | Beard | 233/27 X |
| 3,519,201 | 7/1970 | Eisel et al. | 233/21 |
| 4,094,461 | 6/1978 | Kellogg et al. | 233/40 |
| 4,283,276 | 8/1981 | Grant | 209/155 |
| 4,353,795 | 10/1982 | Romanauskas | 209/155 |
| 4,357,235 | 11/1982 | Dilks | 209/155 |

FOREIGN PATENT DOCUMENTS 2843118  4/1979  Fed. Rep. of Germany ..... 233/1 R

*Primary Examiner*—Ralph J. Hill

[57] ABSTRACT

A plastic ring has a circumferential groove formed in its outer peripheral surface. The ring is fitted in a bowl-type centrifuge rotor such that the ring's outer surface contacts the inner wall of the rotor. The channel is defined by the groove and rotor wall. The rotor is filled with a compensating liquid to reduce centrifugal stress on the plastic and to reduce leakage from the channel.

13 Claims, 5 Drawing Figures

APPARATUS AND METHOD FOR SEDIMENTATION FIELD FLOW FRACTIONATION

CROSS-REFERENCE TO RELATED APPLICATIONS AND PATENTS

This application is related to inventions described in U.S. Pat. No. 4,283,276, issued Aug. 11, 1981 to John Wallace Grant, copending application Ser. No. 249,963, filed Apr. 1, 1981 and entitled "Field Flow Fractionation Channel" by William Andrew Romanauskas, copending application Ser. No. 326,157, filed Nov. 30, 1981 and entitled "Sedimentation Field Flow Fractionation Channel and Method" by Dilks et al., copending application Ser. No. 326,158 filed Nov. 30, 1981 and entitled "Sedimentation Field Flow Fractionation Channel" by J. J. Kirkland, and copending application Ser. No. 352,077 filed Feb. 25, 1982 and entitled "Method and Apparatus for Improving Sedimentation Field Flow Fractionation Channels" by William Andrew Romanauskas.

BACKGROUND OF THE INVENTION

Sedimentation field flow fractionation is a versatile technique for the high resolution separation of a wide variety of particulates suspended in a fluid medium. The particulates include macromolecules in the $10^5$ to the $10^{13}$ molecular weight (0.001 to 1 μm) range, colloids, particles, micelles, organelles and the like. The technique is more explicitly described in U.S. Pat. No. 3,449,938, issued June 17, 1969 to John C. Giddings and U.S. Pat. No. 3,523,610, issued Aug. 11, 1970 to Edward M. Purcell and Howard C. Berg.

In sedimentation field flow fractionation (SFFF), use is made of a centrifuge. A thin annular belt-like channel is made to rotate about the axis of the annulus. The resultant centrifugal force causes sample components of higher density than the mobile phase to sediment toward the outer wall of the channel. For equal particle density, because of their higher diffusion rate, smaller particulates will accumulate into a thicker layer against the outer wall than will larger particulates. On the average, therefore, larger particulates are forced closer to the outer wall.

If now the mobile phase or liquid is fed continuously from one end of the channel, it carries the sample components through the channel for later detection at the outlet of the channel. Because of the shape of the laminar velocity profile within the channel and the placement of particulates in that profile, liquid flow causes smaller; particulates to elute first, followed by elution of components in the order of ascending particulate mass.

There are many criteria that a channel should meet in order to provide accurate particulate characterization data in short time periods. One such criteria is that the separating channel must be relatively thin. Unfortunately, this creates many problems in that the walls of the channel also should have a microscopically smooth finish to prevent the particles from sticking to the walls or being trapped in wall crevices. To provide such a microfinish, as well as to permit cleaning of the channel walls, it is desirable to have access to the interior of the channel. This is most easily achieved, as described in the Grant patent and the Romanauskas application, by the use of mating inner and outer rings with a rectangular groove in the face of one or the other rings defining the channel.

A problem encountered when the channel is formed by mating rings is that of leakage of the liquid from the channel. Leakage is caused by the centrifugally induced pressure on the liquid inside the channel tending to force the fluid medium out between the contacting sealing surfaces of the rings. The problem of preventing leakage is difficult at best, and it is particularly difficult to construct a channel that is absolutely free of such leakage. Leaks may occur because the high force field needed for the separation of the smaller particulates and lower molecular weight solutes distorts the channel itself and tends to cause leakage where none would normally exist. Another problem encountered is the inability to easily provide a variety of channels having different widths, thicknesses, lengths, aspect ratios, and the like while maintaining the thickness dimension of the channel absolutely constant during centrifugal operation at the high force fields required.

SUMMARY OF THE INVENTION

According to the method of this invention, particulates suspended in a fluid medium are separated according to their effective masses by the steps of flowing the fluid medium through an annular channel having an annulus axis and defined by the interfacial space or gap between an outer surface of an inner ring and an inner surface of an outer ring, immersing at least the inner ring in a compensating liquid, and subjecting both the channel and compensating liquid to a contrifugal force by rotating the channel and compensating liquid about the axis. Using this method, the compensating liquid tends to reduce the pressure drop at the interface of the ring between the fluid medium within the channel and the compensating liquid and hence leakage of the fluid medium from the channel. This is particularly true if the liquid is selected to have a density approximately the same as that of the separating fluid medium.

Preferably, the inner ring is positioned within an outer ring formed by the inner wall of a bowl-type rotor. The inner ring is formed of a plastic having an effective density ($\phi$) to tensile modulus (E) ratio ($\phi/E$) exceeding that of the outer ring. The effective density $\phi$ of the plastic is the actual density of the plastic minus the density of the bowl-filling liquid. In this manner, the inner ring will expand at a rate equal to or exceeding that of the outer ring when both are subjected to centrifugal force thereby maintaining a channel seal at the interface between the rings. The plastic inner ring is submerged in a liquid thus reducing channel leakage at the ring interface and the tendency of the channel to bulge at the middle because of internal pressure. This reduces stress on the inner ring and permits the use of plastics for constructing the inner ring. Several rings, each having channel grooves of different widths, lengths, thicknesses and aspect ratios, may be constructed. Then, merely by substituting one ring for another, different sized channels are obtained for various separation goals.

An apparatus constructed according to this invention for separating particulates suspended in a fluid medium according to their effective masses includes an annular channel with an annulus axis, means including a bowl-type rotor for rotating the channel about the axis, means for passing the fluid medium circumferentially through the channel, and means for introducing the particulates into the medium for passage through the channel. This channel is improved according to this invention by forming the channel at the interfacial gap between an inner ring and the inner wall of the bowl-type rotor, and adapting the rotor to contain a liquid that covers at least the inner ring, to reduce stresses on the inner ring, thereby to reduce the leakage of the fluid medium from the channel during centrifugation, and to maintain the thickness of the channel constant.

In a preferred embodiment of this invention, the inner ring is formed of a plastic whose effective density-to-tensile-modulus-ratio ($\phi/E$) is equal to or greater than that of the bowl-type rotor. Preferably, the density of the fluid medium and the density of the liquid are selected to be about equal. Under these conditions, the tendency of the channel to leak at the interface and the tendency of the channel to concave or bulge at its midportion during operation is greatly reduced. To prevent leakage at rest, the two rings are constructed to have an interference fit. The resulting channel then is relatively leak-free and maintains a constant thickness even under the relatively large centrifugal force fields required for particulate separations.

BRIEF DESCRIPTION OF THE DRAWINGS

Further advantages and features of this invention will become apparent from the following description wherein:

FIG. 5 is a partially schematic, partially pictorial representation of an SFFF system using apparatus constructed in accordance with this invention.

DETAILED DESCRIPTION OF THE PREFERRED EMBODIMENT

Figure 1:
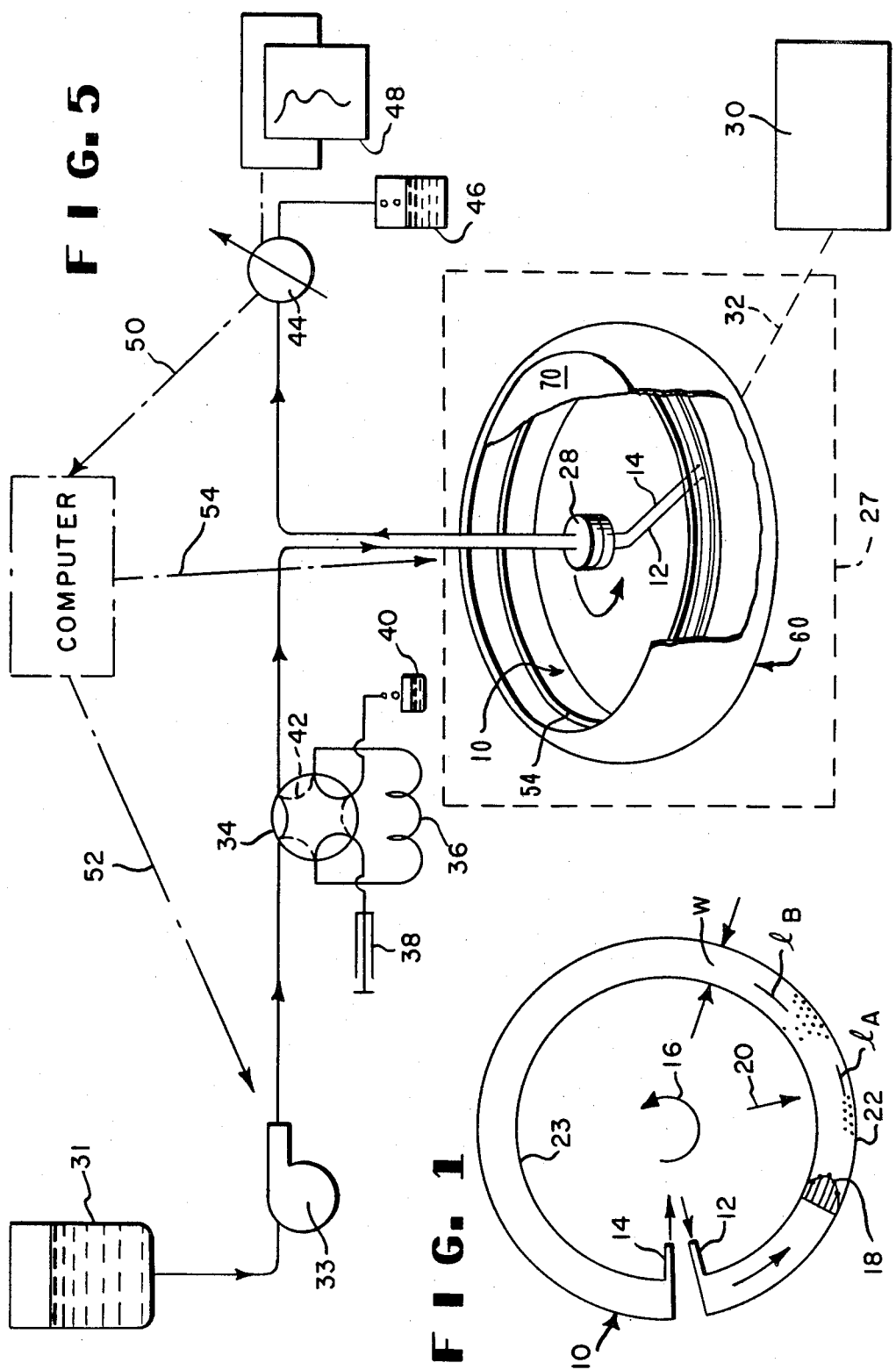
FIG. 1 is a simplified schematic representation of a sedimentation field flow fractionation technique.

The principles of operation of a typical SFFF apparatus with which this invention finds use may perhaps be more easily understood with reference to FIG. 1. In FIG. 1 there may be seen an annular ringlike (even ribbonlike) channel 10 having a relatively small thickness (in the radial dimension) designated W. The channel has an inlet 12 in which the mobile phase or liquid is introduced together with, at some point in time, a small sample containing a particulate to be fractionated, and an outlet 14. The annular channel is spun in either direction. For purposes of illustration, the channel is depicted as being rotated in a counterclockwise direction denoted by the arrow 16. Typically, the thickness of these channels may be in the order of magnitude of 0.025 cm. Actually, the smaller the channel thickness, the greater rate at which separations can be achieved and the greater the resolution of the separations. Alternatively, thicker channels extend the separation range to smaller particles but at the expense of broader peaks.

The channel 10 is defined by an outer surface or wall 22 and an inner surface or wall 23. If now a radial centrifugal force field F, denoted by the arrow 20, is impressed transversely, that is at right angles to the channel, particulates are compressed into a dynamic cloud with an exponential concentration profile, whose average height or distance from the outer wall 22 is determined by the equilibrium between the average force exerted on each particulate by the field F and by the normal opposing diffusion forces due to Brownian motion. Because the particulates are in constant motion at any given moment, any given particulate may be found at any distance from the wall with varying degree of probability. Over a long period of time; compared to the diffusion time, every particulate in the cloud will have been at different heights from the wall many times. However, the average height from the wall of all of the individual particulates of a given mass over that time period will be the same. Thus, the average height of the particulates from the wall will depend on the mass of the particulates, larger particulates having an average height $1_A$ (FIG. 1) that is less than that of smaller particulates $1_B$ (FIG. 1).

If one now causes the fluid in the channel to flow at a uniform speed, there is established a parabolic profile of flow 18. In this laminar flow situation, the closer a liquid layer is to the wall, the slower it flows. During the interaction of the compressed cloud of particulates with the flowing fluid, the sufficiently large particulates will interact with layers of fluid whose average speed will be less than the average for the entire liquid flow in the channel. These particulates then can be said to be retained or retarded by the field or to show a delayed elution from the channel. This mechanism is described by Berg and Purcell in their article entitled "A Method For Separating According to Mass a Mixture of Macromolecules or Small Particles Suspended in a Fluid, I-Theory," by Howard C. Berg and Edward M. Purcell, Proceedings of the National Academy of Sciences, Vol. 58, No. 3, pages 862-869, Sept. 1967.

In accordance with this invention, a continuous inner ring 54 (FIGS. 2, 3 and 4), having a rectangular channel groove or recess 58 formed on its outer peripheral surface is formed of an appropriate engineering plastic such as Delrin ® acetal resin or Noryl ® polyphenylene oxide polymer. This inner ring 54 is inserted into the bowl of a bowl-type centrifuge rotor, such as a zonal rotor 60 such that the lands 59 which define the recess 58 contact the inside polished peripheral surface 63 of the rotor 60. Appropriate O-rings 61, positioned in circumferential grooves 82 formed in the lands 59 on either side of the channel recess 58, provide a backup for the seal of the lands 59. The gap between the recess 58 and the inner surface 63 defines the annular channel 10 which rotates about the axis 62, the axis of the annulus. Due to its inherent elasticity, this plastic inner ring 54 is designed to grow, as will be described below, with the expansion of the zonal rotor 60 as the centrifugal force field is increased.

The rotor 60 is filled with a liquid. This reduces the pressure differences between the fluid medium in the channel 10 and that outside of the channel, thus reducing leakage through the seal at the interface between the inner ring and the rotor bowl. Stress on the plastic inner ring is also reduced because it is surrounded by the liquid. The liquid for filling the rotor bowl and the fluid medium for the channel preferably are selected to have densites that are about equal although fluids with densitites in the range of 0.6 to 1.2 g/ml may be used.

Figure 2:
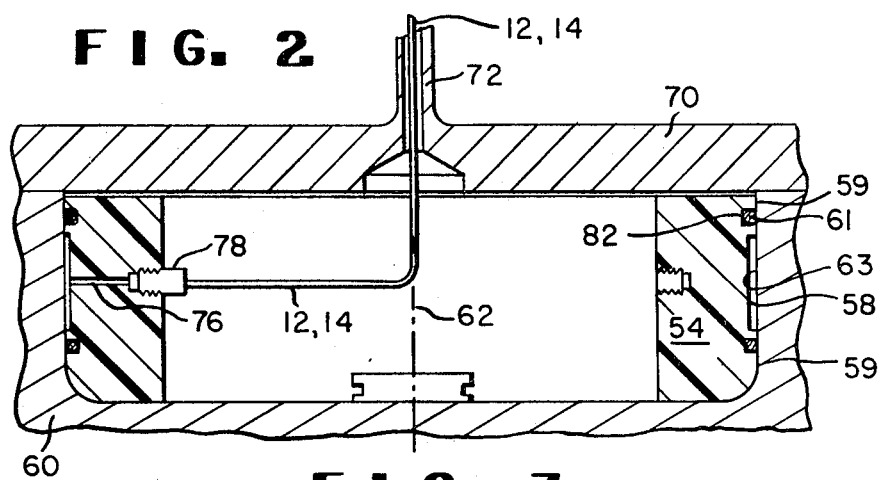
FIG. 2 is a partial cross-sectional elevation view of a continuous inner ring positioned in a zonal rotor to form a flow channel in accordance with this invention.

The construction of this device using a commercial available zonal rotor 60 is depicted in FIG. 2. This rotor is adapted to be driven by a system 30 operating through a linkage 32 to rotate about the axis 62. In this figure, the inner ring 54 is seated in the bottom of the bowl of the zonal rotor 60 which rotates about the axis 62. The rotor 60 has a cover 70 that fastens onto the bowl. A rotating seal 28 (FIG. 5) permits the passage of the fluid medium to and from the channel 10. The rotating seal 28 may be of any conventional design used to couple fluids to and from; rotating bodies such as zonal rotors. The rotating seal described in the Romanauskas application is suitable. Alternatively, the rotating seal described in an application Ser. No. 125,854 filed Feb. 29, 1980 entitled "Drive for Rotating Seal" by Charles Heritage Dilks, Jr. may be used. Whatever the rotating seal used, the conduits 12, 14 (FIG. 2) transmit the fluids from the rotating seal through a hollow drive shaft 72 for the rotating seal 28 (FIG. 5) into the rotor 60 and thence to the channel 10. The drive shaft 72 is secured to the rotor cover 70 and the rotor cover 70 to the rotor 60.

Figure 3:
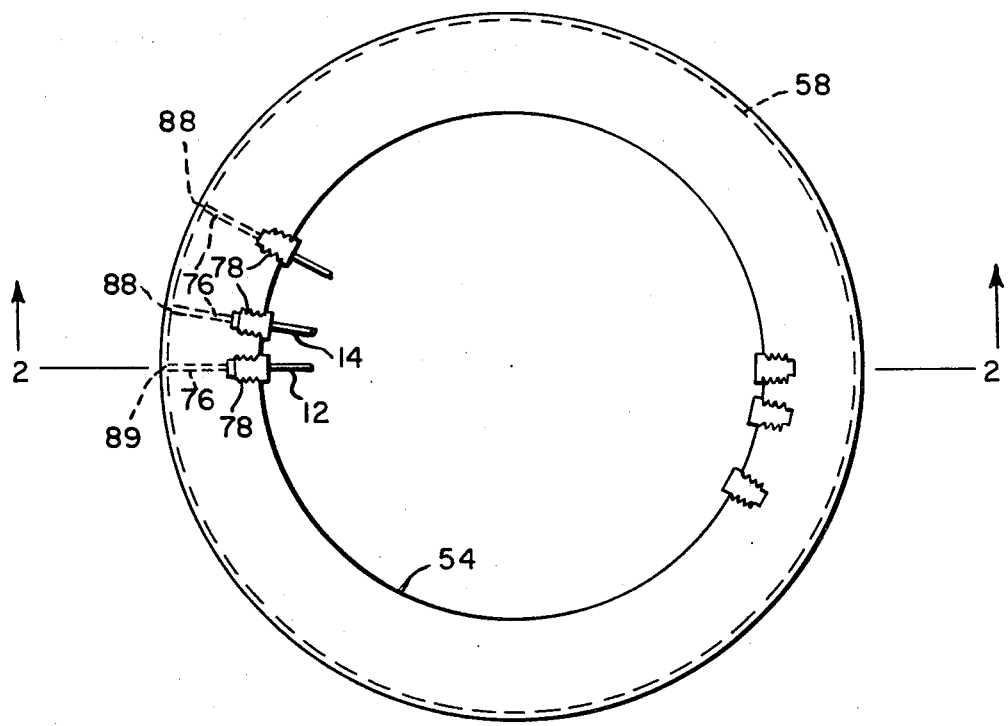
FIG. 3 is a plan view of the inner ring of FIG. 2.

The channel 10 is defined, as described above, by the circumferential recess 58 in the inner ring 54 and the inner wall of the rotor 60 (FIG. 3). The inner ring 54 is formed of a suitable engineering plastic that is chemically inert, strong, and yet resilient such as the two materials mentioned above. Alternatively, the inner ring may be formed of materials such as polytetrafluoroethylene, polyethylene, polyurethane or nylon. One of the main criteria used for selecting the particular engineering plastic for use with high force fields is that its effective density $\phi$ to tensile modulus E ratio generally should exceed the effective density $\phi$ to tensile modulus E ratio of the material forming the rotor 60. The effective density $\phi$ of the plastic is the actual density of the plastic minus the density of the bowl filling liquid. In this manner, as the bowl rotor expands under the influence of centrifugal force, the inner or channel ring 54 expands outwardly a like or slightly greater amount to maintain contact between the lands 59 and O-rings 61 with the inner surface 63 of the rotor 60 and thus to maintain the channel leak-free. The zonal rotor bowl 60, as is typically used in centrifuges, is formed of titanium, stainless steel or aluminum. Titanium is preferred. Preferably, the materials of the rotor bowl and inner ring are selected as described above such that the thickness of the channel is maintained throughout operation within ±2%. This reduces separation errors.

A barrier or dam 86, (FIG. 4) which may be formed of materials such as Mylar ® polyester film or Delrin ® acetyl resin, placed in the recess 58 to define the ends of the channel 10 and may be sealed in position by a suitable cement. The inlet and exit ports 88 and an optional sample inlet 89 for the channel 10 are in the form of bores 76 through the annulus of the inner ring 54. Fittings 78 connect the conduits 12, 14 to the bores 76. The dam 86 is depicted as V-shaped at each end such that dead spaces in the flow path of the fluid medium are reduced and the apex of the V is tangent to the ports 88.

Figure 4:
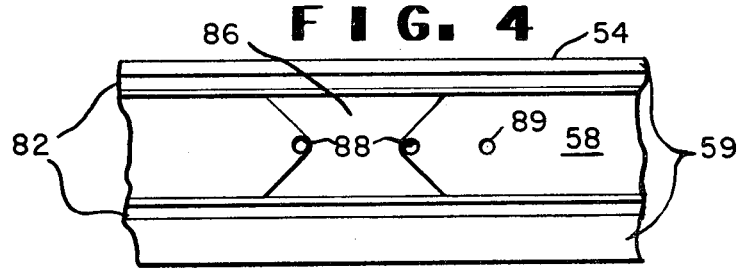
FIG. 4 is a fragmentary side elevation view of a portion of the inner ring depicting the beginning and end of the channel.

The recess 58 formed in the inner ring may be formed to have different depths, different widths, different aspect ratios (width to thickness ratio), lengths, and, if desired, may be formed in a spiral shape. The configuration of the beginning and end of each channel is depicted in FIG. 4. The particular manner in which fluids are fed or withdrawn therefrom are preferably those described in U.S. Pat. No. 4,284,498 issued to Grant et al. on Aug. 18, 1981, the disclosure of which is incorporated herein by reference.

The zonal rotor used to house the inner ring may be that sold by E. I. du Pont de Nemours and Company designated as the TZ-28 Zonal Rotor, an equivalent zonal rotor sold by Beckman Instruments, or any other suitable bowl-type rotor capable of holding liquid and capable of having fluids passed to and from it. The rotating seal described by Dilks has a hollow flexible shaft 72 mounted to the cover 70 of the rotor which provides a drive for the rotating seal 28 (FIG. 5). This flexible shaft aids in decoupling vibrations from the rotor body to the rotating seal and provides a more trouble-free seal. The disclosure of the Dilks application is incorporated herein by reference. Since the particular rotary seal used does not constitute a part of this invention, it will not be described further. Fluids passing through the seal are conducted by suitable flexible tubing such as thin-wall stainless steel tubing 12, 14 through the shaft 72 to the channel assembly. Fluids are fed from the rotating seal through the tubing 12, 14, connectors 78, and bores 76 in the inner ring 54 to the inlet and outlet ports 88 of the channel 10.

In one channel that was successfully built and operated, the inner ring for the rotor assembly was constructed of Delrin 150 plastic with an inner diameter of 13.005 cm, an outer diameter of 17.882 cm, and axial width of 5.080 cm, with a lower corner rounded to a 0.9525 cm radius (to fit in the bowl rotor) and a channel recess 58 having a radial depth of 0.0254 cm and an axial span of 2.54 cm. The rotor was a Beckman Model CF-32Ti and the inner ring was fitted to the polished inner wall of the bowl rotor. This channel was used successfully to separate polystyrene latex standards with narrow particle size distributions. Speeds up to 32000 rpm (approximately 100,000 gravities) were obtained without leakage of the fluid medium in the channel.

According to this invention, the inner ring 54 is formed to have a diametrical interference fit of about 0.076 centimeters (cm) so that the inner wall 63 of the bowl rotor 60 is in constant compressive contact with the lands of the inner ring 54 under static conditions. The very flat lands of the resilient plastic of the inner ring provide a seal for the channel. To aid in maintaining this a seal under operating conditions, the channel recess 58 may be completely surrounded at its periphery by a pair of O-rings (a Viton ® perfluoroelastomer is suitable) 61 which are fitted in grooves 82 formed in the lands 59 of the inner ring 54.

According to the method of this invention, the bowl of the zonal rotor 60 fitted with a channel ring 54 is filled with a liquid of approximately the density as the fluid medium that is pumped through the channel. Under these conditions, when the zonal rotor is rotated, centrifugal force causes the liquid pressure exerted by the liquid in the rotor bowl, external to the channel ring 54, and that exerted internally by the fluid medium within the channel 10, to be about equal. Hence, there is little or no leakage at the interface between the channel ring 54 and the zonal rotor wall 63. Furthermore, there is little tendency of the annulus of the inner ring 54 to buckle inwardly or outwardly either due to the fluid pressure of the fluid medium under centrifugal force or centrifugal force acting on the ring 54. Hence, the thickness of the channel remains relatively constant and plastics may be used for the inner ring. The unique concept of filling the rotor bowl with a liquid outside the plastic ring reduces the tensile strength demands on the plastic material.

With this construction, relatively low cost, precise SFFF channels can be constructed that are capable of accurate particle size analysis and molecular weight determinations under a wide range of operating conditions. Leakage is reduced such that it is essentially eliminated because of the unique construction of the inner ring. Channels having different thicknesses, widths, lengths and aspect ratios may be readily substituted for one another or easily removed for cleaning when required.

For the sake of a complete disclosure, the channels of this invention may be used in the system depicted in FIG. 5. The inlet fluid (or liquid) or mobile phase of the system is derived from suitable solvent reservoirs 31 which are coupled through a conventional pump 33 thence through a two-way, 6-port sampling valve 34 of conventional design through a rotating seal 28, also of conventional design, to the inlet tube 12 of the channel 10, and through the channel 10.

Samples whose particulates are to be separated are introduced into the flowing fluid stream by the sampling valve 34 in which a sample loop 36 has either end connected to opposite ports of the valve 34 with a syringe 38 being coupled to an adjoining port. An exhaust receptacle 40 is coupled to the final port. When the sampling valve 34 is in the position illustrated by the solid lines, sample fluid may be introduced into the sample loop 36 with sample flowing through the sample loop to the exhaust receptacle 40. Fluid from the solvent reservoirs 31 in the meantime flows directly through the sample valve 34. When the sample valve 34 is changed to the second position, depicted by the dashed lines 42, the ports move one position such that the fluid stream from the pump 33 and reservoir 31 now flows through the sample loop 36 before flowing to the rotating seal 28. Thus the sample is carried by the fluid stream to the channel 10.

The outlet line 14 from the channel 10 is coupled back through the rotating seal 28 to a conventional detector 44 and thence to an exhaust or collector receptacle 46. The detector may be any of the conventional types, such as an ultraviolet absorption or a light scattering detector. In any event, the analog electrical output of this detector may be connected as desired to a suitable recorder 48 of known type and in addition may be connected as denoted by the dashed line 50 to a suitable computer for analyzing this data. At the same time this system may be automated, if desired, by allowing the computer to control the operation of the pump 33 and also the operation of the centrifuge 27. Such control is depicted by the dashed lines 52 and 54, respectively.

We claim:

1. In an apparatus for separating particulates suspended in a fluid medium according to their effective masses, said apparatus having an annular cylindrical channel with a cylinder axis, means including a bowl-type centrifuge rotor for rotating said channel about said axis, means for passing said fluid medium circumferentially through said channel, and means for introducing said particulates into said medium for passage through said channel, the improvement wherein:
    said rotor has an inner wall and an inner ring seated in said rotor,
    said channel is defined by the interfacial gap between the inner ring and the inner wall of said bowl-type rotor, and
    said rotor is adapted to contain a liquid that covers said inner ring, thereby to reduce leakage of the fluid medium from said channel during centrifugation.

2. The apparatus of claim 1 wherein said inner ring is plastic.

3. The apparatus of claim 1 or 2 wherein said channel is defined by a rectangular cross-sectioned recess in the mating surface of said inner ring.

4. The apparatus of claim 1 or 2 wherein said channel is defined by a groove in the mating surface of said inner ring and said channel is sealed by sealing members encircling said channel groove.

5. The apparatus of claim 1 or 2 wherein said inner ring and said inner wall have an interference fit, thereby to provide a seal for said channel at rest and to hold the inner ring in position in said rotor.

6. The apparatus of claim 1 or 2 wherein the density of said fluid medium and the density of said liquid are selected to be about equal.

7. The apparatus of claim 1 or 2 wherein the inner ring is formed of a plastic having a ratio of the effective density $\phi$ to the tensile modulus E, equal to or exceeding that of the rotor.

8. The apparatus of claim 7 wherein the density of said fluid medium and the density of said liquid lie in the range of 0.6 to 1.2 gm/ml.

9. A method for separating particulates suspended in a fluid medium according to their effective masses by the steps of:
    flowing the fluid medium through an annular channel having an annulus axis and defined by the interfacial gap between the outer surface of an inner ring and an inner surface of an outer ring,
    covering the inner ring with a liquid, and
    rotating the channel and liquid together about the axis.

10. The method of claim 9 which includes positioning the inner ring within an outer ring formed by the inner wall of a bowl-type rotor.

11. The method of claim 9 or 10 wherein the density of the liquid is selected to be about the same as that of the fluid medium.

12. The method of claim 9 or 10 wherein the inner ring is formed of a plastic.

13. The method of claim 9 or 10 wherein the inner ring is formed of a pastic having a ratio of the effective density $\phi$ to the tensile modulus E equal to or exceeding that of the outer ring.

* * * * *